(12) United States Patent
Simons et al.

(10) Patent No.: US 11,554,044 B2
(45) Date of Patent: Jan. 17, 2023

(54) GLAUCOMA TUBE IMPLANT WITH MODULATED FLOW

(71) Applicant: Oregon Health & Science University, Portland, OR (US)

(72) Inventors: David Simons, Portland, OR (US); Robert Kinast, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 416 days.

(21) Appl. No.: 16/645,536

(22) PCT Filed: Sep. 11, 2018

(86) PCT No.: PCT/US2018/050433
§ 371 (c)(1),
(2) Date: Mar. 9, 2020

(87) PCT Pub. No.: WO2019/051475
PCT Pub. Date: Mar. 14, 2019

(65) Prior Publication Data
US 2020/0276050 A1 Sep. 3, 2020

Related U.S. Application Data

(60) Provisional application No. 62/556,877, filed on Sep. 11, 2017.

(51) Int. Cl.
*A61F 9/007* (2006.01)
(52) U.S. Cl.
CPC .... *A61F 9/00781* (2013.01); *A61F 2210/009* (2013.01); *A61F 2250/007* (2013.01)

(58) Field of Classification Search
CPC ............ A61F 9/00781; A61F 2210/009; A61F 2250/007; A61F 2250/0013
See application file for complete search history.

(56) References Cited

U.S. PATENT DOCUMENTS

| | | | | |
|---|---|---|---|---|
| 6,077,299 | A * | 6/2000 | Adelberg | A61F 9/00781 604/9 |
| 10,039,670 | B2 * | 8/2018 | Ilios | A61M 39/228 |
| 2003/0163079 | A1 * | 8/2003 | Burnett | A61M 27/002 604/9 |
| 2004/0162545 | A1 | 8/2004 | Brown et al. | |
| 2009/0131959 | A1 * | 5/2009 | Rolland | A61F 2/04 128/831 |
| 2011/0066098 | A1 * | 3/2011 | Stergiopulos | A61F 9/00781 604/9 |
| 2012/0184892 | A1 | 7/2012 | Bigler et al. | |
| 2013/0199646 | A1 * | 8/2013 | Brammer | B01L 3/50273 137/833 |
| 2014/0343476 | A1 | 11/2014 | Penhasi | |

FOREIGN PATENT DOCUMENTS

| | | |
|---|---|---|
| WO | 2004-008945 | 1/2004 |
| WO | 2016-127130 | 8/2016 |

* cited by examiner

*Primary Examiner* — Paul B Prebilic
(74) *Attorney, Agent, or Firm* — Schwabe, Williamson & Wyatt, P.C.

(57) ABSTRACT

Disclosed are implantable ocular drainage devices that include a reversible switch mechanism to control flow through the drainage device. The devices include a drainage tube and a reversible, bi-stable switch mechanism that includes first and second stationary magnets spaced apart from one another and a magnetic or ferromagnetic mobile element moveably disposed in a channel in the housing.

19 Claims, 9 Drawing Sheets

ID="N" /># GLAUCOMA TUBE IMPLANT WITH MODULATED FLOW

This application claims the priority benefit of the earlier filing date of U.S. Provisional Patent Application No. 62/556,877, filed Sep. 11, 2017, which is hereby incorporated herein by reference in its entirety.

TECHNICAL FIELD

Embodiments relate to glaucoma, and more specifically, to devices for regulating intraocular pressure.

BACKGROUND

Glaucoma is a common eye disease that results when elevated intraocular pressure (IOP) damages the optic nerve. Glaucoma affects between 60-80 million individuals worldwide, and can result in irreversible blindness. The treatment for glaucoma is to lower IOP and, thereby, preserve the remaining optic nerve. Multiple treatments are available to lower IOP, including topical eye drop medications, lasers, and incisional surgeries such as trabeculectomy, minimally invasive glaucoma surgeries, and implantable drainage devices.

Post-operative hypotony (IOP that is too low) is a serious complication that can result from placement of a drainage device. This complication occurs when a drainage device drains too much aqueous fluid, and the resulting IOP is so low that an eye cannot maintain its form. Hypotony causes poor vision, as the outermost ocular layers, including the retina and choroid, fold and collapse. In this soft, low-pressure state, the eye is at elevated risk for devastating complications, such as a suprachoroidal hemorrhage and hypotony maculopathy.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
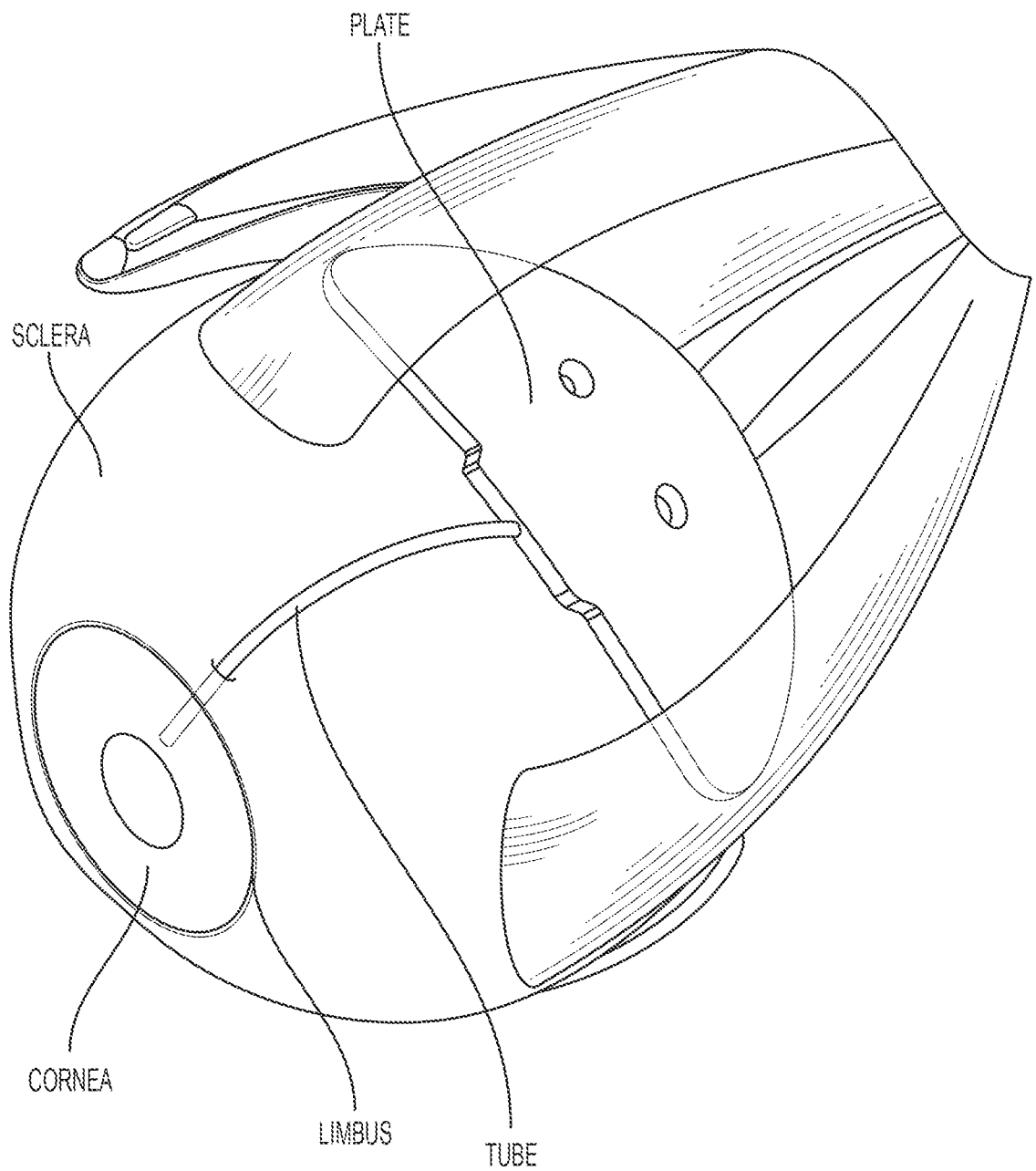
FIG. 1 illustrates a conventional implantable drainage device for reducing IOP.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide reversible mechanisms for non-invasively controlling aqueous flow in implantable drainage devices for the treatment of glaucoma. As disclosed herein, these reversible flow-adjustment mechanisms may result in more predictable control of aqueous flow through an implantable drainage device, such as a drainage tube, and they may reduce post-operative complications, such as hypotony, following surgery to place the drainage device.

In various embodiments, the disclosed flow-adjustment mechanisms may include a magnetically-operated switch mechanism that reversibly adjusts flow through a glaucoma drainage tube. In various embodiments, the flow-adjustment mechanism may include at least two stationary magnets and a mobile element having magnetic or ferromagnetic properties that, together, form a bistable switch in which the mobile element remains in one of the two positions (for example, "on" or "off") until intentionally perturbed by an external magnet.

In some embodiments, when moved into the "off" position, the mobile element may apply lateral pressure to and compress the drainage tube to restrict or block flow through the drainage tube until the mobile element is repositioned to the "on" position, and flow through the drainage tube is restored. In other embodiments, the mobile element may be positioned to occlude an aperture or recess in the drainage tube when moved to the "off" position, and may block flow through the drainage tube until it is returned to the "on" position, away from the aperture or recess, thus restoring flow through the drainage tube. In various embodiments, one of the stationary magnets may retain the mobile element in the "on" position until it is intentionally perturbed by an external magnet. Likewise, another of the stationary magnets may retain the mobile element in the "off" position until it is intentionally perturbed by an external magnet.

Prior to the present disclosure, eye surgeons have used several mechanisms to avoid post-operative hypotony when placing a drainage device such as a drainage tube. For example, when implanting a drainage device, such as the Baerveldt® device (Abbott Medical Optics, Santa Ana, Calif.) shown in FIG. 1, the plate/reservoir is sewn onto the sclera and underneath the conjunctival surface approximately 10 mm posterior to the limbus (corneal border). The tube enters the front of the eye approximately two millimeters behind the limbus, and drains aqueous fluid back to the plate. During the 6-week post-operative period, a capsule of fibrous tissue gradually forms over the plate and progressively limits aqueous flow. However, until the capsule forms there is very little fluid resistance, and an additional flow-restriction mechanism is needed to prevent hypotony.

Such glaucoma drainage devices do not include an internal mechanism that modulates aqueous flow. Therefore, prior to the present disclosure, to avoid early post-operative hypotony, additional time-consuming and problematic mechanisms were used to restrict aqueous flow. For example, a temporary external absorbable suture ligature may be tied around the tube, and/or an internal occluding suture may be placed within the tube. However, to remove an occluding suture post-operatively, a surgeon must make an incision through the conjunctiva; a laser may cut the suture ligature if it does not dissolve on its own. Additionally, outcomes are quite variable with these procedures; aqueous output may be completely restricted, causing dangerously high post-operative IOP, or there may not be enough flow restriction, resulting in vision-threatening hypotony. In the event of high IOP, removal of an occluding suture may lower IOP in an unpredictable manner, and may still result in hypotony.

Other drainage devices, such as the Ahmed® glaucoma valve (New World Medical, Rancho Cucamonga, Calif.), use an intrinsic one-way valve to limit flow, but the valve contributes to a higher failure rate, and early post-operative hypotony still occurs. Both the Ahmed® and Baerveldt® devices have a 40-50% failure rate, with inadequately lowered IOP accounting for about 80% of the Ahmed® device failures, and hypotony or complications like severe vision loss and suprachoroidal hemorrhage accounting for 50% of the Baerveldt device failures.

Figure 2A:
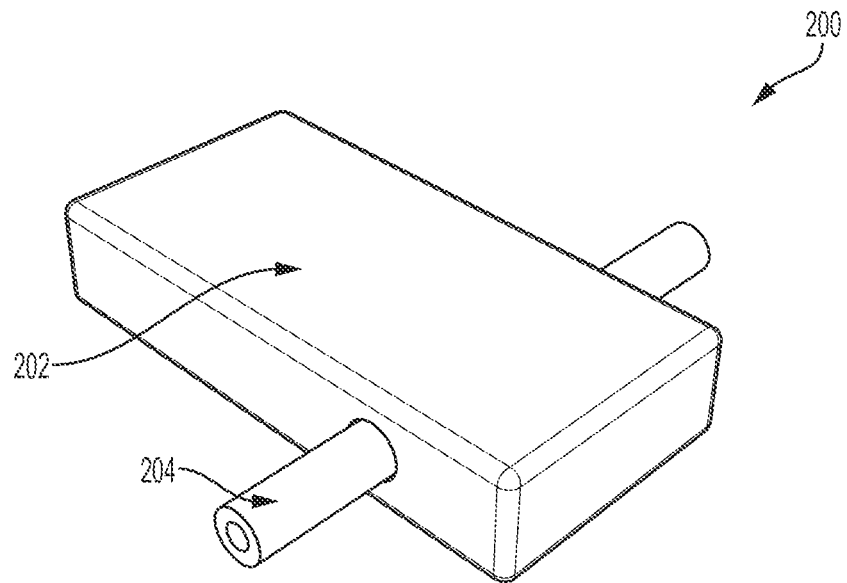
FIGS. 2A and 2B illustrate an embodiment of an implantable drainage device having a reversible mechanism for regulating post-operative flow through the drainage tube, shown with the housing in place (FIG. 2A), and with a portion of the housing removed (FIG. 2B), in accordance with various embodiments.
Figure 2B:
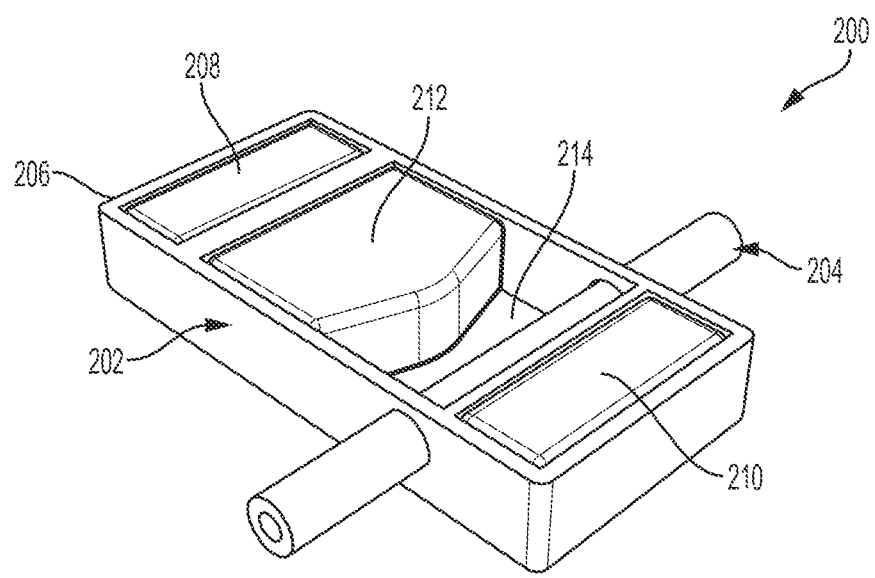

FIGS. 2A and 2B illustrate one embodiment of an implantable drainage device having a reversible mechanism for regulating post-operative flow through the drainage tube, shown with the housing in place (FIG. 2A), and with a portion of the housing removed (FIG. 2B), in accordance with various embodiments. In the embodiment illustrated in FIG. 2A, the implantable drainage device 200 includes a switch mechanism 202 and a drainage tube 204 that passes through a portion of the switch mechanism 202. In FIG. 2B, the drainage device 200 is shown with a portion of the housing 206 enclosing the switch mechanism 202 removed. In the illustrated embodiment, the switch mechanism 202 includes a first stationary magnet 208, a second stationary magnet 210 spaced apart from the first stationary magnet 208, and a mobile element 212 having magnetic or ferromagnetic properties that is slidably disposed between the first and second stationary magnets 208, 210. The mobile element 212 may be urged by an external magnetic force towards the first stationary magnet 208, which retains the mobile element 212 in an "on" position or towards the second stationary magnet 210, which retains the mobile element 212 in an "off" position. In the embodiment illustrated in FIG. 2B, the mobile element 212 is shown in the "on" position, where it exerts no pressure on the drainage tube 204, and it is slidable along a channel 214 defined by a portion of the housing 206. In some embodiments, the drainage tube 204 may be formed from medical grade silicone.

Figure 3A:
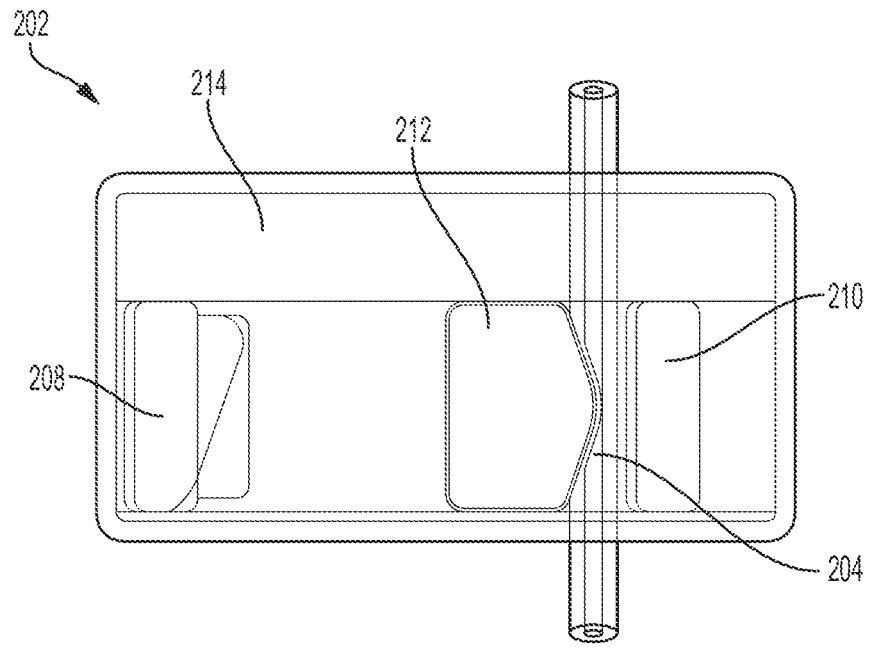
FIGS. 3A and 3B illustrate the operation of the reversible switch mechanism of FIGS. 2A and 2B, with the bistable switch toggled between "off" (FIG. 3A) and "on" positions (FIG. 3B), in accordance with various embodiments.
Figure 3B:
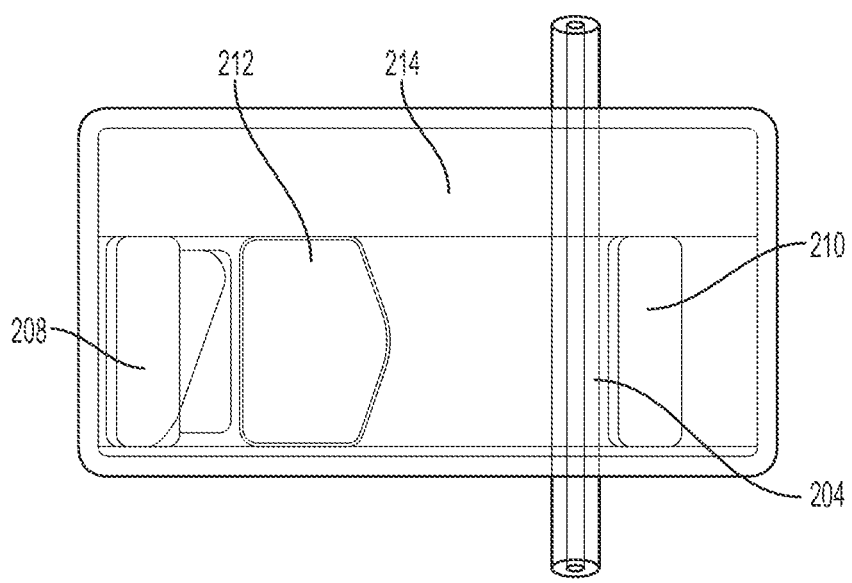

FIGS. 3A and 3B illustrate the operation of the reversible switch mechanism of FIGS. 2A and 2B, with the bistable switch toggled between "off" (FIG. 3A) and "on" positions (FIG. 3B), in accordance with various embodiments. As illustrated, when the mobile element 212 is located at the end of the channel 214, adjacent to the first stationary magnet 208, flow through the drainage tube 204 is freely permitted, and the switch is in the "ON" state. Conversely, when the mobile element 212 is located at the end of the channel 214 near the second stationary magnet 210, adjacent to the drainage tube 204, it applies lateral pressure to the drainage tube 204, which causes the drainage tube 204 to be physically compressed and/or indented, which slows or obstructs flow through the drainage tube 204, and constitutes the "OFF" state. In the illustrated embodiment, the mobile element 212 has a tapered end 216 to allow all of the attractive magnetic force to be concentrated at a single point, making it easier to occlude the drainage tube 204. In some embodiments, a plurality of switch mechanisms 202 may be used together with a single drainage tube 204 to provide additional control over the rate of aqueous humor drainage through the drainage tube 204.

In various embodiments, positioning the stationary magnets 208, 210 at opposite ends of the switch mechanism 204 forms a bi-stable switch mechanism that will retain the mobile element 212 in one of the two positions ("on" or "off" in this case) until intentionally perturbed by an external magnet.

FIGS. 4A-4E illustrate an embodiment of an implantable drainage device having a reversible mechanism for regulating post-operative flow through the drainage tube, shown with a thin anchoring plate (FIG. 4A), with the anchoring plate removed (FIG. 4B), and illustrating the operation of the reversible mechanism with the bistable switch toggled between "on" and "off" positions (FIGS. 4C-4E), in accordance with various embodiments. In the embodiment illustrated in FIG. 4A, the implantable drainage device 400 includes a switch mechanism (not shown) and a drainage tube 404 that passes through a portion of the switch mechanism. A thin anchoring plate 416 anchors the device to the surface of the eye and provides a reservoir for drained aqueous fluid. In some embodiments, the anchoring plate 416 may be formed from medical grade silicone, polypropylene, or another polymer.

Figure 4A:
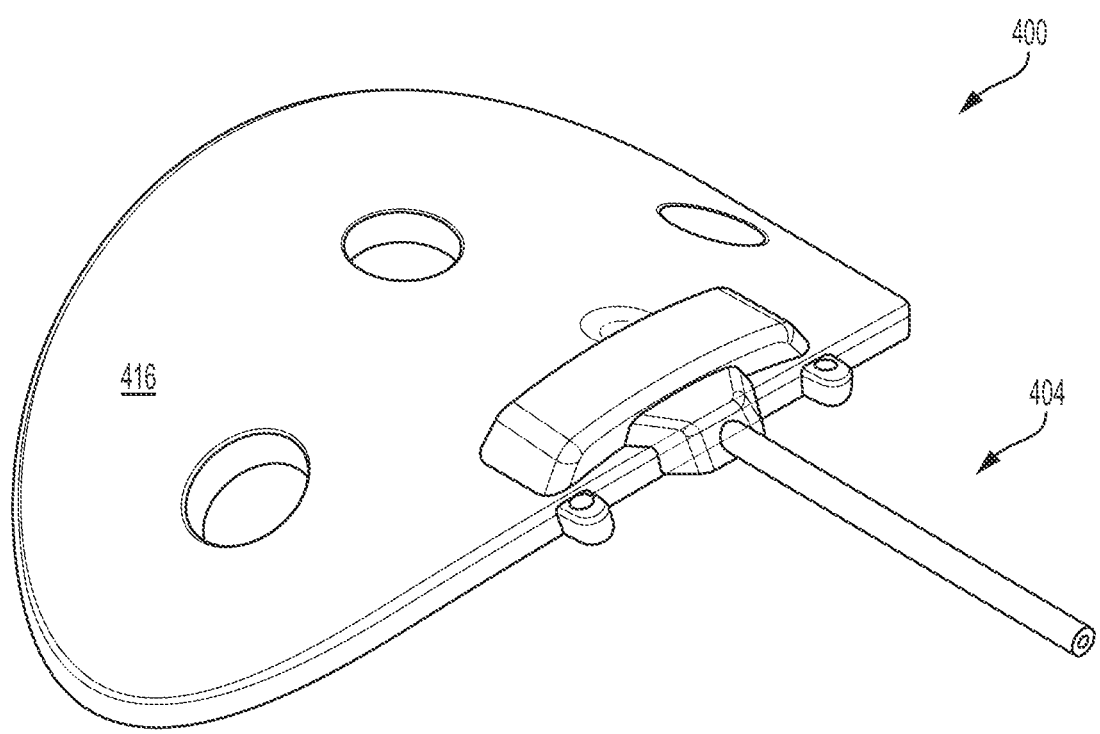
FIGS. 4A-4E illustrate an embodiment of an implantable drainage device having a reversible mechanism for regulating post-operative flow through the drainage tube, shown with a thin anchoring plate in place (FIG. 4A), with the anchoring plate removed (FIG. 4B), and illustrating the operation of the reversible mechanism with the bistable switch toggled between "on" and "off" positions (FIGS. 4C-FIG. 4E), in accordance with various embodiments.
Figures 4C, 4D, 4E:
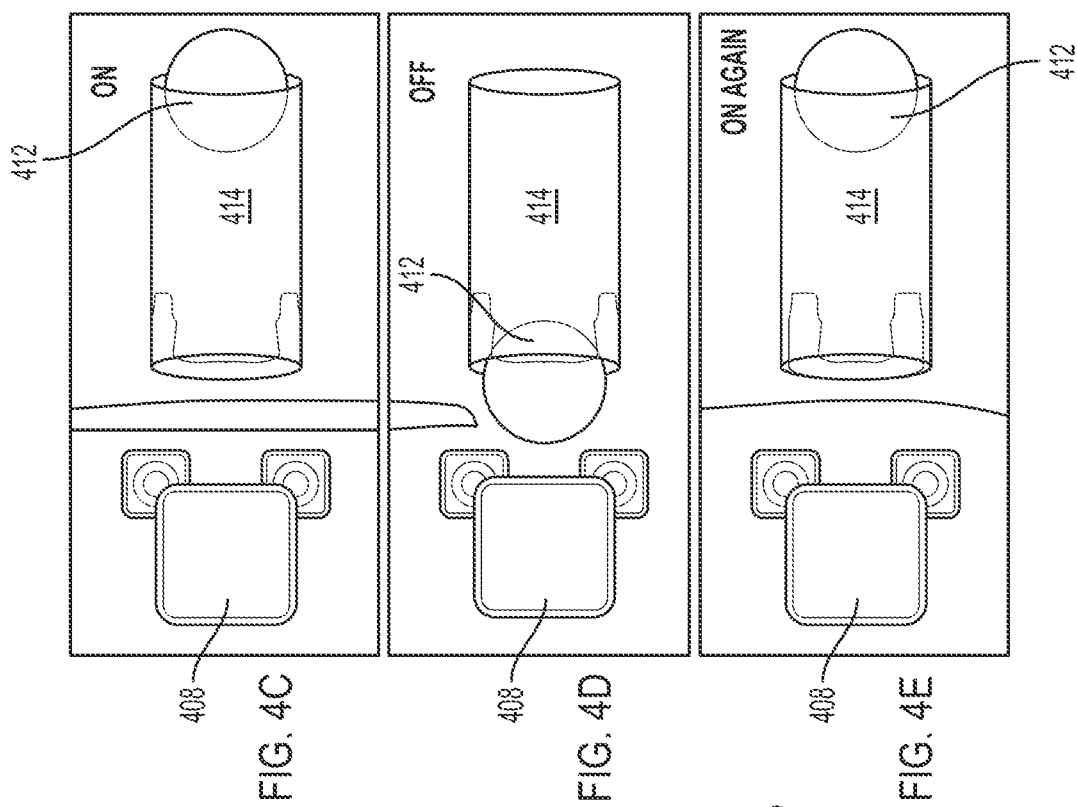
Figure 4B:
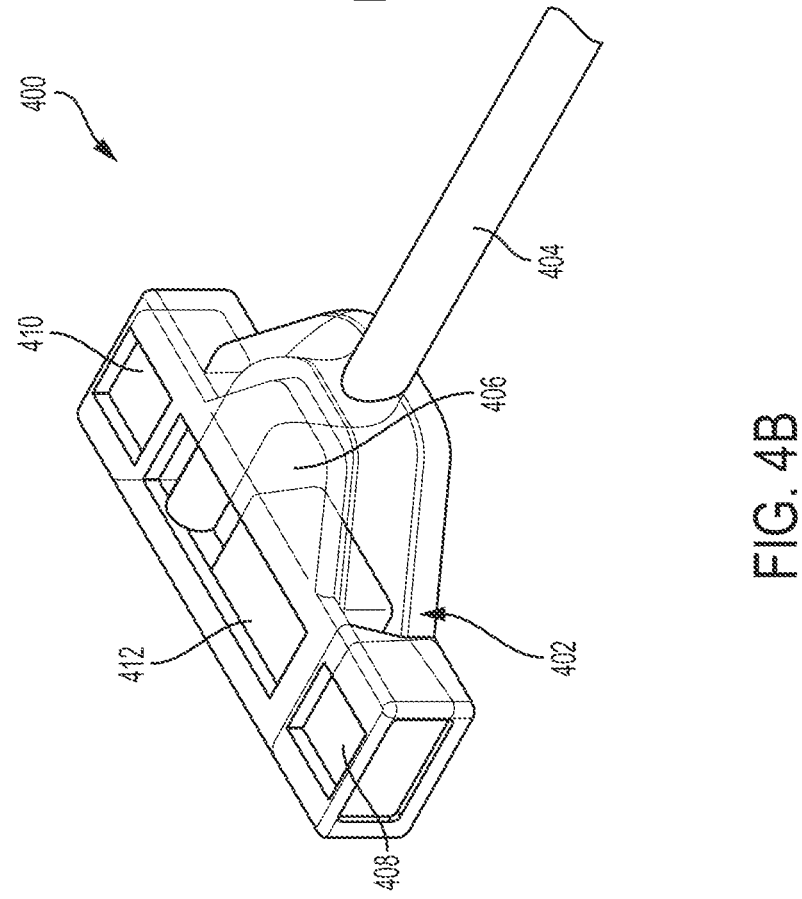

In FIG. 4B, the drainage device 400 is shown with the anchoring plate removed, revealing the switch mechanism 402. In the illustrated embodiment, the switch mechanism 402 includes a first stationary magnet 408, a second stationary magnet 410 spaced apart from the first stationary magnet 208, and a mobile element 412 having magnetic or ferromagnetic properties slidably disposed between the first and second stationary magnets 408, 410. The mobile element 412 may be urged by an external magnetic force towards the first stationary magnet 408, which retains the mobile element 412 in an "on" position or towards the second stationary magnet 410, which retains the mobile element 412 in an "off" position. In the embodiment illustrated in FIG. 4A, the mobile element 412 is shown in the "on" position, where it exerts no pressure on the drainage tube 404. In some embodiments, the magnets 408, 410 and mobile element 412 may be embedded in a plastic housing 406, such as a medical-grade polypropylene housing.

In the embodiment illustrated in FIGS. 4C-4E, the channel 414 may be a hollow tube, and the mobile element 412 may be spherical. When the mobile element 412 is located at the end of the channel 414 adjacent to the first stationary magnet 408, flow is freely permitted and the switch is in the "ON" state (FIGS. 4C and 4E).
Conversely, when the mobile element 412 is located at the end of the channel 414 near the second stationary magnet (not shown) and adjacent to the drainage tube 404, it applies lateral pressure to the drainage tube 404, which causes the drainage tube 404 to be physically compressed and/or indented, which slows or obstructs flow through the drainage tube 404, and constitutes the "OFF" state (FIG. 4D). In alternate embodiments, the drainage device may include a second drainage tube, such as a drainage tube that has a smaller bore and a slower rate of flow compared to the first drainage tube. In these embodiments, the second drainage tube may be open in the "OFF" state, such that a slow rate of flow of aqueous humor may occur even in the "OFF" state. In this state, aqueous fluid is diverted through second drainage tube, whose inner diameter and length are predetermined to achieve a desired minimum pressure. This minimum pressure is high enough to prevent post-operative hypotony.

Figure 5:
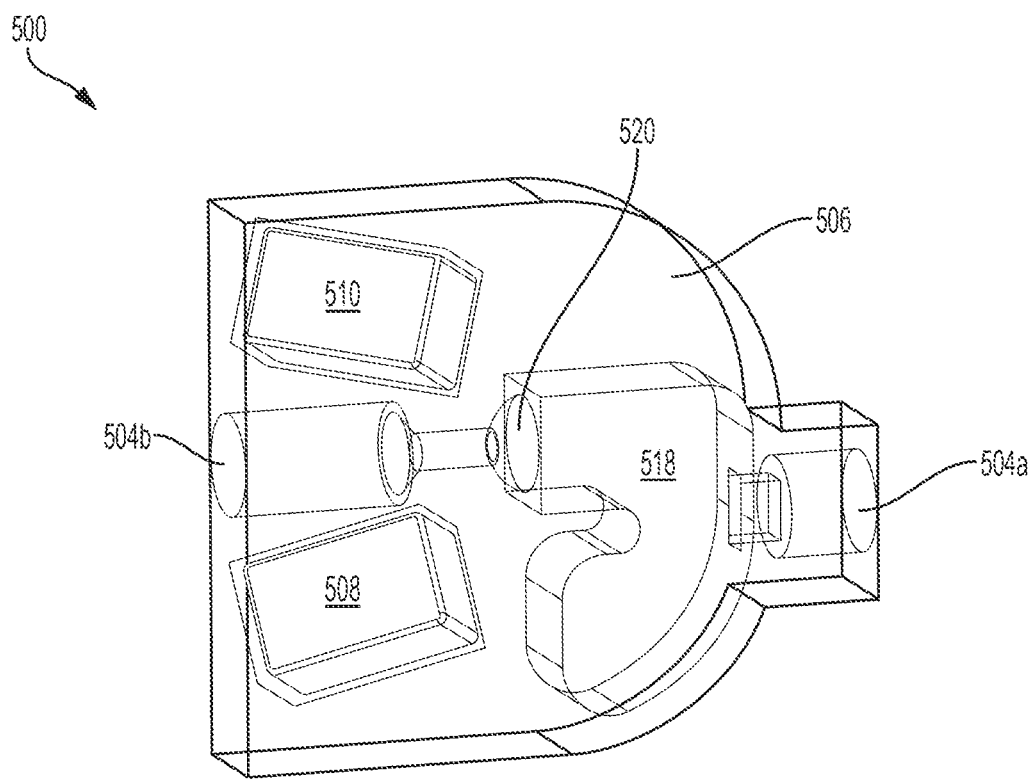
FIG. 5 illustrates an embodiment of an implantable drainage device having a reversible mechanism for regulating post-operative flow through the drainage tube, in accordance with various embodiments.

FIG. 5 illustrates another embodiment of an implantable drainage device having a reversible mechanism for regulating post-operative flow through the drainage tube, in accordance with various embodiments. Like the embodiments depicted in FIGS. 2-4C, the embodiment depicted in FIG. 5 includes a magnetically-operated, bi-stable switch, but the switch operates in a different manner compared to the embodiments described above.

As illustrated in FIG. 5, the drainage device 500 includes a drainage tube inlet 504a and a drainage tube outlet 504b that, together with channel 518, define a fluid path through the housing 506. The drainage device 500 also includes a first stationary magnet 508, a second stationary magnet 510 spaced apart from the first stationary magnet 508, and a spherical mobile element (not shown) having magnetic or ferromagnetic properties that is movably disposed within a channel 518 defined in the housing 506. In use, the drainage tube inlet 504a, drainage tube outlet 504b, and channel 518 are filled with aqueous humor, and the spherical mobile element may be urged by an external magnetic force towards the first stationary magnet 508, which retains the spherical mobile magnet or ferromagnetic ball in the "on" position or towards the second stationary magnet 510, which retains the spherical mobile magnet or ferromagnetic ball in the "off" position. When the spherical mobile element is retained in the "off" position, it occludes a portion of the channel 518 and/or the drainage tube outlet 504b, thus preventing the passage of aqueous humor through the drainage device 500.

Figure 6B:
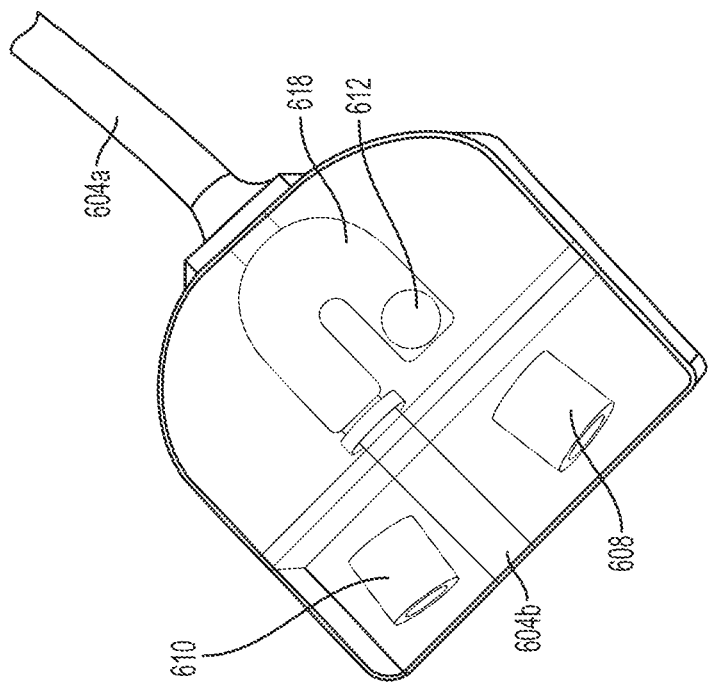
FIGS. 6A and 6B illustrate the operation of the reversible mechanism of FIG. 5, with the bistable switch toggled between "OFF" (FIG. 6A) and "ON" (FIG. 6B) positions, in accordance with various embodiments.
Figure 6A:
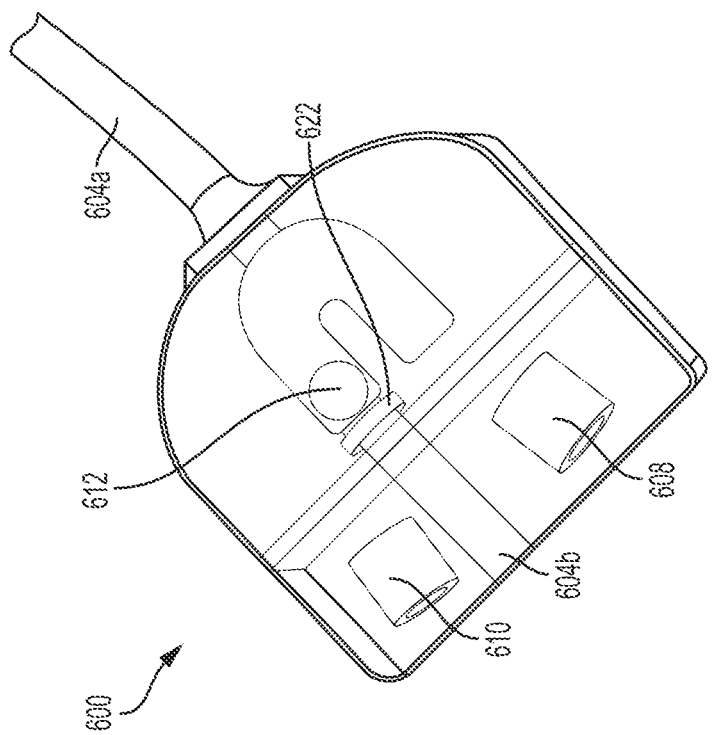

FIGS. 6A and 6B illustrate the operation of a reversable switch mechanism that is similar to the reversible mechanism of FIG. 5, with the bistable switch toggled between "OFF" (FIG. 6A) and "ON" (FIG. 6B) positions, in accordance with various embodiments. As illustrated in FIG. 6A, which depicts the drainage device 600 in the "OFF" state, the spherical mobile element 612 is positioned within the channel 618 over an opening of the drainage tube outlet 604b so that a watertight seal is created, thus preventing the passage of aqueous humor through the drainage device 600. In operation, the spherical mobile element 612 may be urged by an external magnetic force towards the first stationary magnet 608, which retains the spherical mobile element 612 in the "on" position or towards the second stationary magnet 610, which retains the spherical mobile magnet or ferromagnetic ball in the "off" position. When the spherical mobile element 612 is retained in the "off" position, it occludes a portion of the channel 618 and/or the drainage tube outlet 604b, thus preventing the passage of aqueous humor through the drainage device 600. In the illustrated embodiment, a silicone O-ring 622 is used to create the water-tight seal. In other embodiments, such as the embodiment shown in FIG. 5, a recess 520 in the precision-machined plastic housing 506 is provided in the form of a hemi-spherical depression that is sized to receive and form a watertight seal with the spherical mobile element.

As illustrated in FIG. 6B, the spherical mobile element 612 may be drawn by an external magnetic force to the opposite side of the aqueous-filled channel 618, thus allowing flow through the outlet tubing once again ("ON" state). An advantage of the embodiments illustrated in FIGS. 5, 6A, and 6B is that the design permits the use of smaller magnets (e.g., 608, 610) to be used, thus making the device less susceptible to the effects of an MRI machine. In some embodiments, the spherical mobile element may be a spherical magnet or ferromagnetic ball, such as a steel ball, in direct contact with the aqueous humor. Because surgical stainless steel is poorly ferromagnetic, to prevent oxidation of the spherical mobile element 612, a conformal coating of non-reactive material such as parylene or PTFE may be to be included on the surface of the spherical mobile element.

Figure 7:
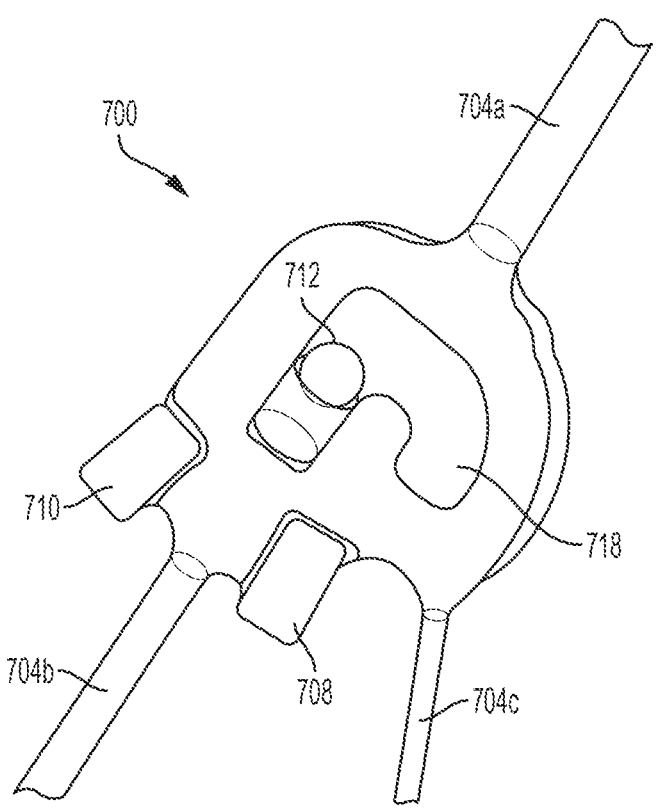
FIG. 7 illustrates an embodiment of an implantable drainage device having a reversible mechanism for regulating post-operative flow through the drainage tube, in accordance with various embodiments.

FIG. 7 illustrates another embodiment of an implantable drainage device having a reversible mechanism for regulating post-operative flow through the drainage tube, in accordance with various embodiments. As illustrated, the drainage device 700 includes a drainage tube inlet 704a, a first drainage tube outlet 704b, and a second drainage tube outlet 704c that, together with channel 718, define a fluid path through the housing. The drainage device 700 also includes a first stationary magnet 708, a second stationary magnet 710 spaced apart from the first stationary magnet 708, and a spherical mobile element 712 having magnetic or ferromagnetic properties that is movably disposed within a channel 718 defined in the housing. In use, the drainage tube inlet 704a, first drainage tube outlet 704b, second drainage tube outlet 704c, and channel 718 are filled with aqueous humor, and the spherical mobile element 712 may be urged by an external magnetic force towards the first stationary magnet 708, which retains the spherical mobile magnet or ferromagnetic ball in the "high flow" position. Urging the spherical mobile magnet or ferromagnetic ball towards the second stationary magnet 710 retains the spherical mobile magnet or ferromagnetic ball in the "low flow" position. When the spherical mobile element 712 is retained in the "low flow" position, it occludes a portion of the channel 718 and/or the first drainage tube outlet 704b, thus preventing the passage of aqueous humor through the first drainage tube outlet 704b.

The second drainage tube outlet 704c has a smaller inner bore or lumen compared to the first drainage tube outlet 704b, and remains open in the "low flow" state. When the drainage device is in the "low flow" position, and the first drainage tube outlet 704b is occluded by the spherical mobile element 712, the pressure in the system will gradually build. In this state, aqueous fluid is diverted through second drainage tube outlet 704c, whose inner diameter and length are predetermined to achieve a desired minimum pressure.

Figure 8:
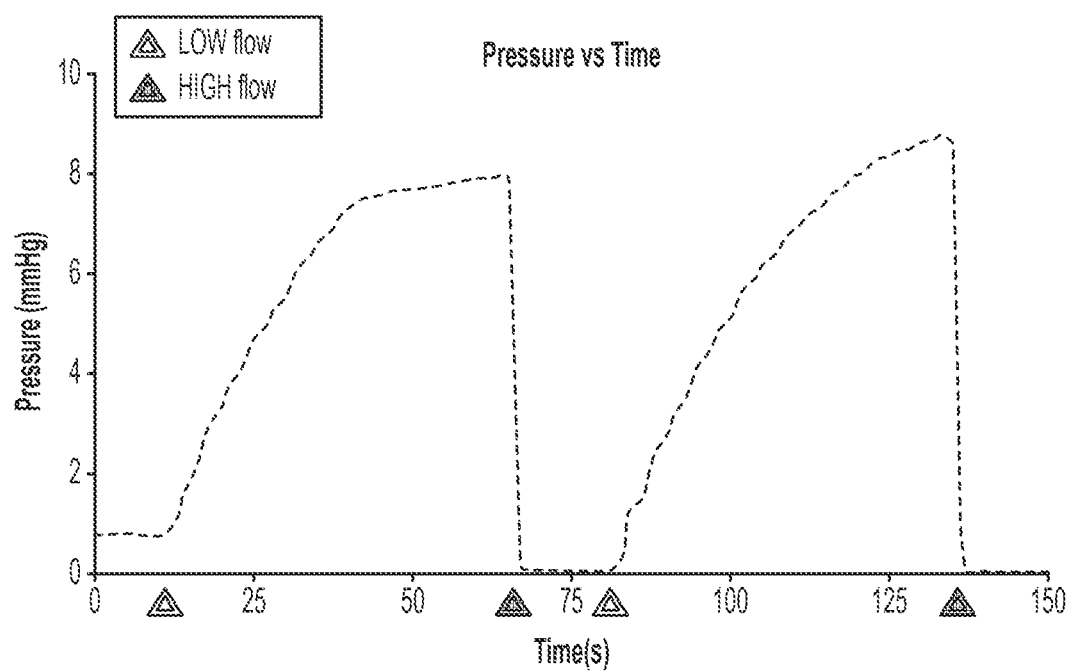
FIG. 8 is a graph, showing the in vitro pressure levels generated by the implantable drainage device of FIG. 7, in accordance with various embodiments.

FIG. 8 is a graph, showing the pressure levels generated by the implantable drainage device of FIG. 7 in vitro, in accordance with various embodiments. As illustrated, the pressure in the system begins to build when the switch is moved into the "low flow" position. In this state, aqueous fluid is diverted through the second drainage tube outlet, which has an inner diameter and length that are predetermined to achieve a minimum pressure in accordance with Pouiselle's law. This minimum pressure is high enough to prevent post-operative hypotony.

In the "high flow" state, aqueous humor is allowed to flow through the first drainage tube outlet without any flow restriction. As illustrated, the pressure drops to essentially zero because there is no intrinsic flow restriction. However, in a post-surgical situation, there would be a fibrotic capsule forming around the plate of the device, which restricts flow to a certain degree, and which acts as the primary determinant of the post-operative eye pressure when the system is in the "high flow" state.

The purpose of the "low-flow" state is to provide a modest amount of pressure lowering immediately after tube implantation, but with enough flow restriction to prevent the IOP from dropping too low (e.g., hypotony). The dimensions (inner diameter and length) of the second drainage tube outlet may be modified according to the Hagen-Poiseuille equation to achieve an appropriate amount of flow restriction, and therefore a theoretical "floor" for the eye pressure during the early post-operative period. This theoretical "floor" is greater than the typical range of eye pressures in which clinical hypotony is observed, which is roughly 0 to 7 mmHg. In some embodiments, the theoretical floor may be selected to be higher than this range, such as about 8, 9, 10, 11, 12, 13, 14, or 15 or more mmHg, such as about 11-13 mmHg, or about 12 mmHg.

Figure 9:
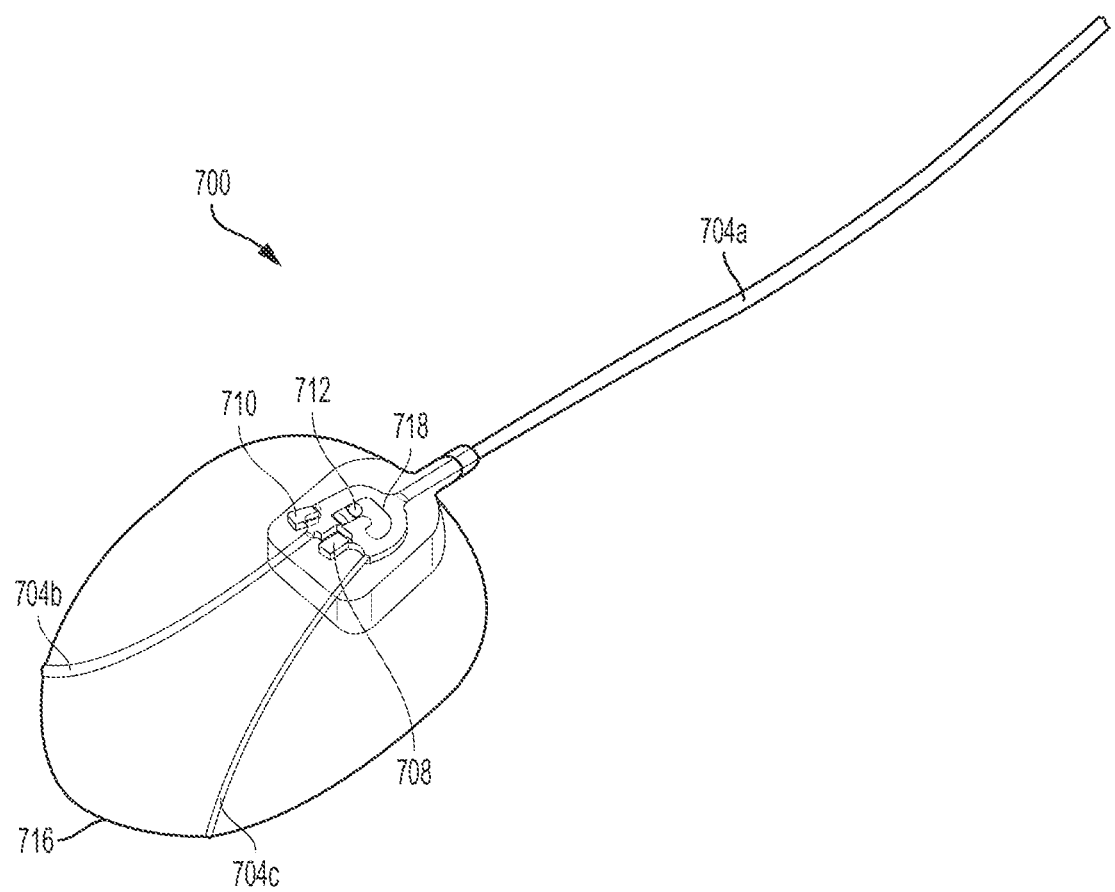
FIG. 9 illustrates the implantable drainage device of FIG. 7, shown with a thin anchoring plate in place, in accordance with various embodiments.

FIG. 9 illustrates the implantable drainage device of FIG. 7, shown with a thin anchoring plate in place, in accordance with various embodiments. FIG. 9 illustrates the spatial relationships between various components of the drainage device 700, including the anchoring plate 716, drainage tube inlet 704a, first drainage tube outlet 704b, second drainage tube outlet 704c, channel 718, first stationary magnet 708, second stationary magnet 710, spherical mobile element 712." Although the first and second drainage tube outlets are illustrated in a particular configuration, one of skill in the art will appreciate that the location and/or orientation of these elements may be different in other embodiments.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An implantable ocular drainage device comprising:
a first drainage tube having a drainage tube inlet and a first drainage tube outlet;
a housing comprising a reversible, bi-stable switch mechanism and at least a portion of the drainage tube, the bi-stable switch mechanism comprising:
a first stationary magnet fixedly disposed in the housing;
a second stationary magnet fixedly disposed in the housing, wherein the second stationary magnet is spaced apart from the first stationary magnet;
a mobile element having magnetic or ferromagnetic properties and moveably disposed in a channel in the housing, wherein the mobile element is movable between a first position and a second position;
wherein the first stationary magnet retains the mobile element in the first position unless an external magnetic force is applied to the mobile element;
wherein the second stationary magnet retains the mobile element in the second position unless an external magnetic force is applied to the mobile element; and
wherein the mobile element at least partially occludes the first drainage tube when the mobile element is in the second position, and does not occlude the first drainage tube when the mobile element is in the first position.

2. The device of claim 1, wherein the mobile element is magnetic.

3. The device of claim 2, wherein the channel is disposed between the first stationary magnet and the second stationary magnet.

4. The device of claim 3, wherein the channel comprises an elongated void having a first end and a second end, wherein the first end is adjacent to the first stationary magnet and the second end is adjacent to the second magnet.

5. The device of claim 4, wherein the mobile element applies lateral pressure to and compresses the first drainage tube when the mobile element is retained in the second position.

6. The device of claim 5, wherein the mobile element reduces a flow of an aqueous humor through the first drainage tube when retained in the second position.

7. The device of claim 4, wherein the mobile element may be moved from the first position to the second position, and from the second position to the first position by application of an external magnetic force.

8. The device of claim 1, further comprising a second drainage tube, wherein the second drainage tube remains open when the mobile element is in the second position.

9. The device of claim 1, wherein the mobile element is a ferromagnetic sphere.

10. The device of claim 9, wherein the channel is in fluid communication with the drainage tube inlet and the first drainage tube outlet.

11. The device of claim 10, wherein the channel comprises a curved void having a first end and a second end, wherein the first end is adjacent to the first stationary magnet and the second end is adjacent to the second magnet.

12. The device of claim 11, wherein the moveable element occludes the first drainage tube outlet when the moveable element is retained in the second position in the second end of the channel.

13. The device of claim 12, wherein the second end of the channel comprises an O-ring positioned to form a watertight seal with the mobile element when the mobile element is retained in the second position.

14. The device of claim 12, wherein the second end of the channel comprises a hemispherical depression sized and shaped to form a watertight seal with the mobile element when the mobile element is retained in the second position.

15. The device of claim 12, wherein the mobile element prevents flow of aqueous humor from the drainage tube inlet to the first drainage tube outlet when retained in the second position.

16. The device of claim 10, wherein the mobile element may be moved from the first position to the second position, and from the second position to the first position, by application of an external magnetic force.

17. The device of claim 10, wherein the mobile element is coated with a non-reactive coating.

18. The device of claim 1, further comprising a second drainage tube outlet, and wherein aqueous humor is permitted to flow through the second drainage tube outlet when the mobile element is in the second position.

19. The device of claim 18, wherein the second drainage tube outlet is sized to permit a minimum rate of flow of aqueous humor, and wherein the minimum rate of flow is sufficient to prevent hypotony.

\* \* \* \* \*